United States Patent [19]

Chapleo et al.

[11] 4,411,908
[45] Oct. 25, 1983

[54] IMIDAZOLINE DERIVATIVES AS PRESYNAPTIC $\alpha_2$-ADRENORECEPTOR ANTAGONISTS

[75] Inventors: Christopher B. Chapleo, Swanland; Peter L. Myers, Princes Risborough, both of England

[73] Assignee: Reckitt & Colman Products Limited, London, England

[21] Appl. No.: 397,686

[22] Filed: Jul. 13, 1982

[30] Foreign Application Priority Data

Jul. 28, 1981 [GB] United Kingdom ................ 8123271

[51] Int. Cl.³ .................. A61K 31/415; C07D 405/04
[52] U.S. Cl. ............................. 424/273 R; 548/348; 549/467; 549/468
[58] Field of Search ..................... 548/348; 424/273 R

[56] References Cited
U.S. PATENT DOCUMENTS 3,927,023 12/1975 Brown et al. ....................... 548/348

OTHER PUBLICATIONS

Shridhar, D. et al., Indian Journal of Chemistry, 18B, 254–256, (1979).

Primary Examiner—Richard A. Schwartz
Attorney, Agent, or Firm—Bacon & Thomas

[57] ABSTRACT

Imidazoline derivatives of the formula

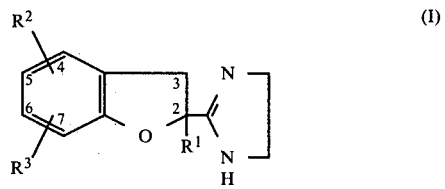

wherein
 $R^1$ is hydrogen or alkyl $C_{1-6}$;
 $R^2$ is hydrogen, methyl, chloro, bromo or fluoro;
 $R^3$ is hydrogen, methyl, hydroxy, methoxy, fluoro, chloro or bromo; and their non-toxic salts.

Processes for their preparation and pharmaceutical compositions thereof. The compounds exhibit presynaptic $\alpha_2$-adrenoreceptor antagonist activity.

13 Claims, No Drawings

IMIDAZOLINE DERIVATIVES AS PRESYNAPTIC α₂-ADRENORECEPTOR ANTAGONISTS

This invention relates to imidazoline derivatives, their non-toxic salts, processes for their preparation and pharmaceutical compositions of the derivatives or their salts.

Indian Journal of Chemistry 18B, 254–256 (1979) discloses benzofuran substituted at the 2-position by amidine, substituted amidine, 2-imidazolinyl or 2-tetrahydropyrimidinyl groups. The compounds were evaluated for antibacterial and antifungal activity without showing any note-worthy activity. Selected compounds were also tested for anti-inflammatory activity. One of the compounds disclosed but not evaluated for anti-inflammatory activity was 2-(2-benzofuranyl)-2-imidazoline of formula:

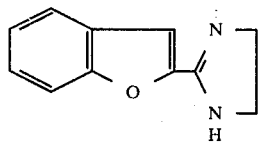

(A)

We have now prepared and evaluated a novel series of 2-[2-(2,3-dihydrobenzofuranyl)]-2-imidazolines which we have shown to possess presynaptic α₂-adrenoreceptor antagonist properties.

According to this invention there are provided compounds of the formula:

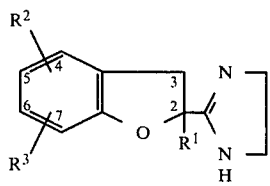

(I)

wherein
$R^1$ is hydrogen or alkyl $C_{1-6}$;
$R^2$ is hydrogen, methyl, chloro, bromo or fluoro;
$R^3$ is hydrogen, methyl, hydroxy, methoxy, fluoro, chloro or bromo; and their non-toxic salts.

In an aspect of the invention in the compounds of formula I
$R^1$ is hydrogen or alkyl $C_{1-6}$;
$R^2$ is hydrogen and $R^3$ is methyl, hydroxy, methoxy, fluoro, chloro or bromo; or
$R^2$ and $R^3$ are the same and both are hydrogen, methyl or chloro; and their non-toxic salts.

It will be appreciated that the compounds of formula I contain an asymmetric carbon atom and it is to be understood that the invention includes both the racemic mixtures and the optically active enantiomers. Unless otherwise indicated, the specific compounds of the invention herein described are all in the racemic form.

The invention also includes a pharmaceutical compositions comprising a compound of formula I or a non-toxic salt thereof, together with a pharmaceutically acceptable diluent or carrier.

Examples of non-toxic salts are those with inorganic acids such as hydrochloric acid, sulphuric or phosphoric acid; or organic acids such as acetic, propionic, malonic, succinic, fumaric, tartaric, citric or cinnamic acid. A preferred salt is the hydrochloride.

The adrenoreceptors of the sympathetic nervous system have for many years been classified into two main types namely alpha ($\alpha$) and beta ($\beta$). In recent years this classification has needed to be modified since subgroups of each type have been identified making the full classification $\alpha_1$, $\alpha_2$ and $\beta_1$, $\beta_2$. Both $\beta_1$ and $\beta_2$ as well as $\alpha_1$ adrenoreceptors are situated primarily on the surface of smooth muscle cells (postsynaptic). In contrast $\alpha_2$-adrenoreceptors have been shown by many workers to be situated predominantly on the nerve terminals (presynaptic) of noradrenergic nerves. These receptors when stimulated under physiological conditions by the natural transmitter, noradrenaline, inhibit its exocytotic release. Thus, presynaptic adrenoreceptors initiate a negative feed-back loop which regulates transmitter concentration within the synaptic gap.

Selective antagonism of $\alpha_2$-adrenoreceptors would inhibit the negative feedback loop which becomes operational on the release of noradrenaline from the sympathetic nerve endings. Such an inhibition would result in an increase in the synaptic concentration of noradrenaline with a consequent augmentation of the activity of the sympathetic nervous system. Such a drug would be predicted to be of value in conditions which have been postulated to be associated with a deficiency of available noradrenaline at postsynaptic adrenoreceptor sites in the central and/or peripheral nervous system. These conditions include endogenous depression, cardiac failure and conditions associated with excessive bronchoconstriction such as asthma and hay fever.

It has been suggested recently that glucose and lipid metabolism can be controlled either directly or indirectly (via insulin) by an inhibitory mechanism involving $\alpha_2$-adrenoreceptors (Berthelsen & Pettinger, Life Sciences, 1977, 21, 595). $\alpha_2$-Adrenoreceptor antagonists may have a role to play therefore in the control of metabolic disorders such as diabetes and obesity.

The proximal tubules of the guinea-pig kidney are rich in $\alpha_2$-adrenoreceptors, the activation of which leads to sodium retention (Young & Kuhar, Eur. J. Pharmac., 1980, 67, 493). This suggests that $\alpha_2$-adrenoreceptor antagonists may produce diuresis and hence the compounds may have utility as diuretics.

Presynaptic α-adrenoreceptors have also been implicated in humoral processes. For example it has been demonstrated that $\alpha_2$-adrenoreceptor agonists initiate, and antagonists inhibit, human platelet aggregation (Grant, J. A., and Scrutton, M. C., Nature, 1979, 277, 659). Thus a presynaptic $\alpha_2$-adrenoreceptor antagonist may be clinically desirable in pathogenic conditions in which increased platelet aggregation is implicated, for example, migraine. Hannington (Lancet, 1978, 2, 501) proposed that an abnormality of platelet function leading to increased aggregation was the prime cause of migraine attacks. Therefore selective antagonists of presynaptic $\alpha_2$-adrenoreceptors may afford prophylactic protection in migraine. Additionally, the acute effect of the classical antimigraine compound ergotamine has been attributed to its postsynaptic $\alpha_1$-adrenoreceptor agonist activity (Hokkanen et al., Headache, 1978, May, 95). Hence, compounds possessing both presynaptic α-adrenoreceptor antagonist and postsynaptic $\alpha_1$-adrenoreceptor agonist properties might be particularly useful in the acute and prophylactic treatment of migraine.

The invention also includes the use of a compound of formula I or a non-toxic salt thereof in the treatment of depression and a method of treating depression which comprises administering to humans an antidepressant effective amount of a compound of formula I or a non-toxic salt theref.

The invention also includes the use of a compound of formula I or a non-toxic salt thereof in the treatment of migraine and a method of treating migraine which comprises administering to humans an antimigraine effective amount of a compound of formula I or a non-toxic salt thereof.

The compounds of formula I wherein $R^1$ is hydrogen or alkyl $C_{1-6}$; $R^2$ is hydrogen, methyl, chloro, bromo or fluoro; and $R^3$ is hydrogen, methyl, methoxy, fluoro, chloro or bromo may be prepared from the analogous compounds of formula II

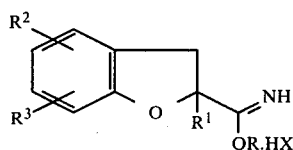
(II)

wherein R is alkyl $C_{1-4}$ and HX is an acid (preferably a pharmaceutically acceptable acid) by treatment with at least one molar equivalent of ethylenediamine. Preferably the reaction is carried out in a polar solvent such as methanol or ethanol. Preferably R is methyl or ethyl, HX is hydrogen chloride and the reaction is carried out in methanol or ethanol respectively.

The compounds of formula II may be prepared from the analogous cyano compounds of formula III

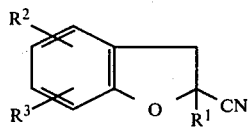
(III)

by treatment with an alcohol of formula ROH, wherein R is as hereinbefore defined, in the presence of an acid HX where HX is as hereinbefore defined. Most conveniently the alcohol employed is methanol or ethanol and HX is hydrogen chloride.

A particularly convenient method of preparing the compounds of formula I by the above process is to generate the compound of formula II in situ from the cyano compound of formula III. Thus for example a cyano compound of formula III dissolved in an alcohol of formula ROH (e.g. methanol or ethanol) is treated with a sodium alkoxide RONa (e.g. sodium methoxide or ethoxide), followed by reaction with hydrogen chloride (conveniently dissolved in an alcohol ROH e.g. methanol or ethanol) and at least one molar equivalent of ethylenediamine.

The compounds of formula I in which $R^3$ is hydroxy may be prepared from the analogous compounds of formula I in which $R^3$ is methoxy by hydrolysis with a dealkylating reagent such as aqueous hydrobromic acid.

The cyano compounds of formula III may be prepared from the analogous amido compounds:

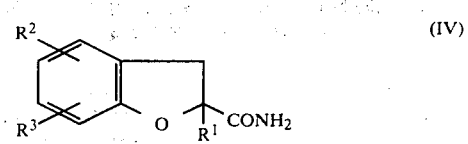
(IV)

by dehydration with for example phosphorus pentoxide or phosphorus oxychloride.

The amido compounds of formula IV may be prepared by treating the analogous acid chlorides with ammonia. The acid chlorides in turn having been prepared from the analogous acids V by treatment with a halogenating agent such as thionyl chloride in a solvent such as toluene.

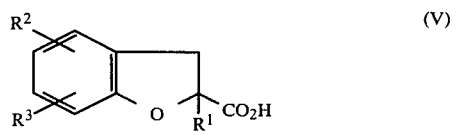
(V)

The acids of formula V wherein $R^1=H$ may be prepared from the corresponding unsaturated acids of formula VI by reduction for example using a reagent such as sodium amalgam. The acids of formula VI

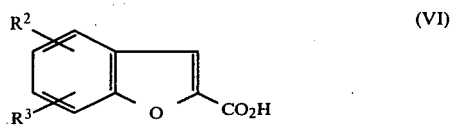
(VI)

may be prepared by reacting salicylaldehyde of formula VII

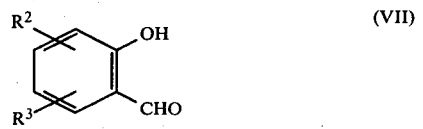
(VII)

with diethyl bromomalonate in the presence of a base such as potassium carbonate followed by hydrolysis of the intermediate ester.

The acids of formula V wherein $R^1=$ alkyl $C_{1-6}$ may be prepared by direct alkylation of the analogous acids of formula V, wherein $R^1=H$, with the alkyl halide in the presence of a base such as lithium diisopropylamide.

The acids of formula V wherein $R^1=$ hydrogen or alkyl $C_{1-6}$ may also be prepared from the alcohols of formula VIII by oxidation using a reagent such as potassium permanganate.

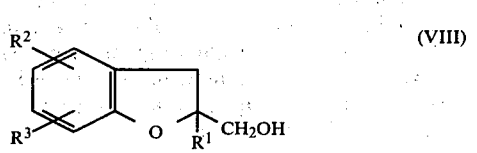
(VIII)

The alcohols of formula VIII may be prepared from the phenols of formula IX

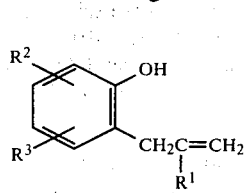

by oxidation with a peracid such as m-chloroperbenzoic acid or peracetic acid and cyclisation of the intermediate epoxides of formula X by acid catalysis or by heating.

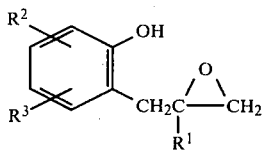

The invention is illustrated by the following Examples in which temperatures are in degrees Celsius.

The various compounds and intermediates were examined by thin layer chromatography (t.l.c.) on silica gel plates (Merck, Kieselgel 60 $F_{254}$) using diethyl ether/light petroleum (40°–60°) (1:1) as eluent. Melting points were determined on a Kofler hot stage apparatus or a Buchi apparatus in glass capillary tubes and are uncorrected. I.R. spectra were recorded on a Perkin-Elmer 710B spectrophotometer.

EXAMPLE 1

2-[2-(5-Fluoro-2,3-dihydrobenzofuranyl)]-2-imidazoline hydrochloride (a) 5-Fluorobenzofuran-2-carboxylic acid 5-Fluorosalicylaldehyde (4.4 g), diethylbromomalonate (11.3 g) and methyl ethyl ketone (35 ml) were stirred together. Anhydrous potassium carbonate (8.7 g) was added and the mixture was heated at reflux for 4 hours. Excess dilute sulphuric acid was added and the mixture was extracted with diethyl ether. The combined extracts were washed with water, dried and evaporated to leave an oil which was treated with 10% w/v ethanolic KOH (60 ml) and heated at reflux for 45 minutes. The solvent was evaporated and the residue treated with excess dilute sulphuric acid and heated briefly on a steam bath. After cooling the crude acid was filtered off. Recrystallisation from ethylacetate/ethanol gave a fawn coloured product (1.1 g), m.p. 261°–266° (decomp), I.R. $\nu_{max}$ 1685 cm$^{-1}$.

(b) 5-Fluoro-2,3-dihydrobenzofuran-2-carboxylic acid

5-Fluorobenzofuran-2-carboxylic acid (2.4 g) was added to aqueous sodium hydroxide solution (3.3 g of sodium hydroxide in 50 ml of water). Sodium amalgam was added over 20 minutes (prepared from 1.1 g of sodium and 42 g of mercury). After a further 2½ hours the solution was left to stand over the amalgam overnight. The mercury was separated and the solution filtered and then treated with excess 4 M sulphuric acid. The precipitated acid was filtered off and dried over $P_2O_5$ in vacuo (1.5 g) I.R. $\nu_{max}$ 1720 cm$^{-1}$.

(c) 5-Fluoro-2,3-dihydrobenzofuran-2-carbonyl chloride

Thionyl chloride (1.1 ml) was added to a suspension of 5-fluoro-2,3-dihydrobenzofuran-2-carboxylic acid (1.4 g) in anhydrous toluene (12 ml). The mixture was heated at 90°–100° with stirring for 2 hours and then the solvent and excess thionyl chloride were removed in vacuo to leave the acid chloride as an oil (~1.5 g) I.R. $\nu_{max}$ 1820 cm$^{-1}$.

(d) 5-Fluoro-2,3-dihydrobenzofuran-2-carboxamide

A solution of 5-fluoro-2,3-dihydrobenzofuran-2-carbonyl chloride (1.5 g) in anhydrous dioxan (6 ml) was added dropwise to a stirred, cooled (0°–10°) solution of ammonia (9 ml, d 0.88). After completion of the addition the mixture was allowed to warm up to room temperature and water (40 ml) was added. The solid was collected by filtration and recrystallized from ethanol to yield the carboxamide (0.8 g) I.R. $\nu_{max}$ 1660 cm$^{-1}$ $R_f$(ethyl acetate) 0.33.

(e) 2-Cyano-5-fluoro-2,3-dihydrobenzofuran

A suspension of 5-fluoro-2,3-dihydrobenzofuran-2-carboxamide (0.8 g) in anhydrous toluene (42 ml) was treated with phosphorus pentoxide (3.1 g) and the mixture was heated at reflux with stirring for 3 hours. The cooled solution was decanted off and the residue washed with additional toluene. The combined toluene fractions were washed with water, dried and evaporated to leave the cyano compound as a solid (0.4 g) $R_f$(ethyl acetate) 0.65.

(f) 2-[2-(5-Fluoro-2,3-dihydrobenzofuranyl)]-2-imidazoline hydrochloride

Sodium methoxide (0.01 g) was added with stirring to a solution of 2-cyano-5-fluoro-2,3-dihydrobenzofuran (0.35 g) in methanol (2 ml). After 18 hours at room temperature the solution was cooled to 0° and a solution of ethylene diamine (0.16 g) in methanol (1 ml) was added dropwise. After 15 minutes a solution of hydrochloric acid in methanol (~1.1 molar equivalents of HCl) was added dropwise with cooling. After 2 hours the methanol was removed in vacuo and the residue was partitioned between chloroform and saturated aqueous sodium bicarbonate solution. The free base was extracted with chloroform and the combined extracts washed with water and dried. Ethereal hydrogen chloride was added to the chloroform extracts followed by diethyl ether and the precipitated salt was collected by filtration (0.44 g) m.p. 209°–219° (decomp).

EXAMPLE 2

2-[2-(5-Methoxy-2,3-dihydrobenzofuranyl)]-2-imidazoline hydrochloride

This was prepared from 5-methoxy-2,3-dihydrobenzofuran-2-carboxylic acid by the methods c-f of Example 1 and had m.p. 209°–211° (decomp).

EXAMPLE 3

2-[2-(5-Hydroxy-2,3-dihydrobenzofuranyl)]-2-imidazoline hydrobromide

The free base generated from 2-[2-(5-methoxy-2,3-dihydrobenzofuranyl)]-2-imidazoline hydrochloride (1.5 g) was treated with 48% w/v hydrobromic acid solution (15 ml) and the mixture heated at ~100° for 7 hours with stirring. Evaporation of the solvent gave a solid residue which was recrystallized from ethanol/diethyl ether to yield the required imidazoline hydrobromide (0.5 g) m.p. 231°–235°.

EXAMPLE 4

2-[2-(2-Methyl-2,3-dihydrobenzofuranyl)]-2-imidazoline hydrochloride (a) 2-Methyl-2,3-dihydrobenzofuran-2-carboxylic acid This was prepared by two alternative methods.

A. (i) 1-(2-Hydroxyphenyl)-2-methyl-2,3-epoxypropane

A solution of m-chloroperbenzoic acid (72.8 g) in methylene chloride (900 ml) was added dropwise over 3 hours to a stirred solution of 3-(2-hydroxyphenyl)-2-methylprop-1-ene (48.1 g) in methylene chloride (450 ml) cooled in an ice-water bath to 10°–20°. The mixture was stirred for a further 24 hours and was then filtered to remove m-chlorobenzoic acid. The filtrate was washed successively with a 10% w/v aqueous solution of sodium sulphite (500 ml), saturated aqueous sodium bicarbonate solution and finally with saturated brine. The organic phase was dried and evaporated in vacuo to give the desired epoxide (52.7 g); $R_f$ 0.37

(ii) 2-Hydroxymethyl-2-methyl-2,3-dihydrobenzofuran

A mixture of 1-(2-hydroxyphenyl)-2-methyl-2,3-epoxypropane (52.7 g) and silica (Kieselgel 60; 70–230 mesh) (150 g) in methylene chloride (300 ml) was stirred at room temperature for 24 hours. Removal of the solvent gave a residue of silica and absorbed product and this mixture was stirred with ethyl acetate for 3 hours. After filtration the ethyl acetate filtrate was dried and the solvent evaporated in vacuo to give the desired alcohol 49.6 g. This crude product was dissolved in methylene chloride and washed with 1 N aqueous sodium hydroxide solution, water and then dried. Removal of the solvent gave the alcohol as a yellow oil 37 g; I.R. $\nu_{max}$ 3700-3200 cms$^{-1}$.

(iii) 2-Methyl-2,3-dihydrobenzofuran-2-carboxylic acid

The 2-hydroxymethyl-2-methyl-2,3-dihydrobenzofuran (16.4 g) and potassium hydroxide (5.2 g) in water (150 ml) were mixed and cooled to 5°. Potassium permanganate (20 g) was added portionwise over 45 minutes to the stirred mixture maintained below 12°. After the addition was complete stirring was continued for 1 hour and the mixture was then diluted with water. Sodium metabisulphite was added to destroy the precipitated $MnO_2$ followed by an excess of sodium carbonate. The basic aqueous phase was washed with methylene chloride and then acidified with 2 N hydrochloric acid. Extraction with methylene chloride followed by washing, drying and evaporation of the extracts gave the carboxylic acid (3.0 g); I.R. $\nu_{max}$ 1720 cm$^{-1}$.

B. 2-Methyl-2,3-dihydrobenzofuran-2-carboxylic acid

A dry argon filled flask was charged with di-isopropylamine (8.1 g freshly distilled from calcium hydride) and tetrahydrofuran (120 ml) freshly distilled from LiALH$_4$ via a syringe septum cap. The stirred solution was cooled to −78° using a methanol/CO$_2$ bath. n-Butyllithium (1.6 M in hexane; 55 ml) was added dropwise over 5–10 minutes and the mixture allowed to return to room temperature. On recooling to −78°, a solution of 2,3-dihydrobenzofuran-2-carboxylic acid (3.3 g in tetrahydrofuran (30 ml) was added dropwise with the immediate formation of an orange-red solution. After 20 minutes methyliodide (10 g; freshly dried by passing down a silica column and distilling) was quickly added with an almost instantaneous loss of colour (pale yellow solution). After 45 minutes the mixture was poured onto ice and extracted with methylene chloride (3×75 ml). The extracts were dried and evaporated to give the crude carboxylic acid (3.5 g), (identical by N.M.R. and t.l.c. to that by method A).

(b) 2-[2-(2-Methyl-2,3-dihydrobenzofuranyl)]-2-imidazoline hydrochloride

This was prepared from 2-methyl-2,3-dihydrobenzofuran-2-carboxylic acid by the methods c-f of Example 1 and had m.p. 268°–270°.

Table 1 gives details of further compounds of formula I in which $R^1$ is hydrogen, prepared by the method f of Example 1 or in the case of Examples 22 and 23 by the method of Example 3.

TABLE 1

| EX | $R^1$ | $R^2$ | salt | m.p. °C. |
|---|---|---|---|---|
| 5 | H | 5-Cl | HCl | 225–250(d) |
| 6 | H | H | HCl | 204–210(d) |
| 7 | H | 4-Me | HCl | 237–238 |
| 8 | H | 4-Cl | HCl | 233–237 |
| 9 | H | 5-Me | HCl | 214–224 |
| 10 | H | 5-Br | HCl | 216–246(d) |
| 11 | H | 6-Me | HCl | 230–240 |
| 12 | H | 6-OMe | HCl | 224–228 |
| 13 | H | 7-Me | HCl | 271–274 |
| 14 | H | 7-OMe | HCl | 230–250(d) |
| 15 | H | 7-Cl | HCl | 220–270(d) |
| 16 | 4-Me | 7-Me | HCl | 254–257 |
| 17 | 5-Me | 6-Me | HCl | 215–216 |
| 18 | 5-Me | 7-Me | HCl | 230–253(d) |
| 19 | 5-Cl | 7-Cl | HCl | 279–281 |
| 20 | 6-Cl | 7-Cl | HCl | 308–310 |
| 21 | 5-Cl | 7-Me | HCl | 245–266(d) |
| 22 | H | 6-OH | HBr | 249–254 |
| 23 | H | 7-OH | HBr | 234–241 |

Me = methyl;
d = decomposition temperature.

The pharmacological activity of the compounds of the invention have been determined according to the following procedures.

1. Pre- and postsynaptic α-adrenoreceptor antagonism in isolated tissue experiments Initial biological evaluation of presynaptic $\alpha_2$-adrenoreceptor antagonism was assessed by determining pA$_2$ values against the inhibitory effects of clonidine, a well known presynaptic α-adrenoreceptor agonist, on the rat vas deferens stimulated at a frequency of 0.1 Hz according to the method of Doxey, J. C., Smith, C. F. C., and Walker, J. M., Br. J. Pharmac., 1977, 60, 91.

This in vitro model is particularly useful as an initial screen for studying presynaptic activity in isolation since the physiological nature of the vas deferens tissue is such that the postsynaptic receptors located therein are particularly inaccessible to exogenous agents. In consequence an alternative tissue, the rat anococcygeus muscle is used to establish postsynaptic α-adrenoreceptor activity. Antagonism of noradrenaline contractions is used to determine pA$_2$ values at postsynaptic α-adrenoreceptors. The ratio of presynaptic α-adrenoreceptor antagonism (versus clonidine on the rat vas deferens) to postsynaptic α-adrenoreceptor antagonism (versus noradrenaline contractions on the rat anococcygeus muscle) is used to assess adrenoreceptor selectivity. Table 2 shows the results for the compound of Example 5 (I; $R^1=R^2=H$, $R^3=5$-Cl) and the results for four standard drugs: (i) the non-selective α- adrenoreceptor antagonist, phentolamine, (ii) the selective presynaptic antagonist, yohimbine, (iii) the highly selective postsynaptic antagonist, prazosin and (iv) the antidepressant, mianserin which shows non-selective pre- and postsynaptic adrenoreceptor antagonist properties as part of its pharmacological profile.

TABLE 2

| Compound | Presynaptic antagonism $pA_2$ vs Clonidine (vas deferens) | Postsynaptic antagonism $pA_2$ vs Noradrenaline (anococcygeus) | Pre/post synaptic ratio |
| --- | --- | --- | --- |
| Example 5 | 8.2 | 6.2 | 100 |
| Phentolamine | 8.4 | 7.7 | 4.8 |
| Yohimbine | 8.2 | 6.4 | 60 |
| Prazosin | 5.9 | 8.2 | 0.005 |
| Mianserin | 7.3 | 6.6 | 5.0 |

The results are the mean of a minimum of 5 experiments.

2. Presynaptic α-adrenoreceptor antagonism in the pithed rat

Rat vas deferens-intravenous activity.

This test model extends the evaluation of presynaptic α-adrenoreceptor antagonism versus clonidine on the rat vas deferens to the in vivo situation. Stimulation-induced contractions of the vas deferens were monitored in pithed rats using the method of Brown, J., Doxey, J. C., Handley, S. and Virdee, N., Recent Advances in the Pharmacology of Adrenoceptors, Elsevier North Holland, pp. 367–370, 1978. Clonidine (100 μg/kg, i.v.) causes a prolonged pressor response and a prolonged inhibition of vas deferens contractions. The test drugs were injected intravenously in a cumulative dosing schedule and their abilities to reverse the inhibition of hypogastric nerve stimulation reflected their presynaptic antagonism. Table 3 shows the doses of antagonists which caused a 50% reversal of the inhibition of hypogastric nerve stimulation.

TABLE 3

| Relative antagonist potencies at presynaptic α-adrenoreceptors in the pithed rat | |
| --- | --- |
| Compound | i.v. dose of antagonist causing 50% reversal of clonidine block on vas deferens mg/kg |
| Example 5 | 0.102 |
| Yohimbine HCl | 0.86 |
| Mianserin HCl | >4.4 |
| Phentolamine mesylate | 0.12 |

The results are the mean of a minimum of 4 rats.

Under the chosen experimental conditions, all of the compounds studied, with the exception of mianserin, produced a complete reversal of the inhibitory effects of clonidine on hypogastric nerve stimulation. The maximum reversal seen with mianserin was 36% at a cumulative intravenous dose of 4.4 mg/kg. It can be seen in Table 3 that the compound of Example 5 and phentolamine are approximately equipotent against the in vivo presynaptic α-adrenoreceptor stimulant effects of clonidine. In contrast to in vitro data, which demonstrates that yohimbine and the compound of Example 5 possess similar potencies as presynaptic α-adrenoreceptor antagonists (see Table 2), the latter compound is approximately 8 times more potent than yohimbine in pithed rats (Table 3).

3. Presynaptic α-adrenoreceptor antagonist and postsynaptic α-adrenoreceptor agonist activity in isolated tissue experiments The compound of Example 6 is an example of a compound which possesses both presynaptic α-adrenoreceptor antagonist and postsynaptic α-adrenoreceptor agonist properties. Presynaptic α-adrenoreceptor antagonism was determined as described in section 1. Postsynaptic α-adrenoreceptor agonist activity was expressed as a $pD_2$ value which is the negative logarithm of the molar concentration of compound giving 50% maximum contraction in this instance, of the anococcygeus muscle (Brown, J., Doxey, J. C., and Handley, S., Eur. J. Pharmac. 1980, 67, 33). Table 4 gives results for the compound of Example 6 (I, $R^1=R^2=R^3=H$), the analogous dehydro compound of formula A and the postsynaptic agonist activities of clonidine and phenylephrine.

TABLE 4

| Compound | Presynaptic antagonism $pA_2$ vs clonidine (vas deferens) | Postsynaptic agonism $pD_2$ (anococcygeus) |
| --- | --- | --- |
| Example 6 | 8.50 | 6.3 |
| Compound A | 6.08 | — |
| Clonidine | — | 7.5 |
| Phenylephrine | — | 6.5 |

The results are the mean of a minimum of 3 experiments and show that the compound of Example 6 is as a presynaptic $\alpha_2$ antagonist more than 200 times as potent as the analogous dehydro compound. The dehydro compound is in fact a postsynaptic antagonist with a $pA_2$ of 5.24 when tested in the rat anococcygeus muscle.

4. Presynaptic α-adrenoreceptor antagonist and post-synaptic α-adrenoreceptor agonist activity in the pithed rat In vivo presynaptic α-adrenoreceptor antagonist activity was determined using the methods outlined in section 2. Postsynaptic α-adrenoreceptor agonist activity was determined in a separate group of naive pithed rats and was expressed as the intravenous dose of compound which produced an increase in diastolic blood pressure of 50 mmHg. The results obtained are shown in Table 5.

TABLE 5

| Compound | i.v. dose causing 50% reversal of clonidine block on vas deferens mg/kg | i.v. dose causing 50 mmHg increase in diastolic blood pressure mg/kg |
| --- | --- | --- |
| Example 6 | 0.030 | 0.020 |
| Clonidine | — | 0.003 |
| Phenylephrine | — | 0.030 |

In conclusion it can be seen that in both isolated tissues and intact animals the compound of Example 6 displays presynaptic α-adrenoreceptor antagonist properties. Additionally, it is slightly more potent than phenylephrine as a postsynaptic α-adrenoreceptor agonist.

The pharmaceutical compositions may be in a form suitable for oral, rectal or parenteral administration. Such oral compositions may be in the form of capsules, tablets, granules or liquid preparations such as elixirs, syrups or suspensions.

Tablets contain a compound of formula I or a non-toxic salt thereof in admixture with excipients which are suitable for the manufacture of tablets. These excipients may be inert diluents such as calcium phosphate, microcrystalline cellulose, lactose, sucrose or dextrose; granulating and distintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or Kaolin in a hard gelatin capsule.

Compositions for parenteral administration may be in the form of sterile injectable preparations such as solutions or suspensions in for example water, saline or 1,3-butane diol.

For the purposes of convenience and accuracy of dosing the compositions are advantageously employed in a unit dosage form. For oral administration the unit dosage form contains from 1 to 200 mg, preferably 10 to 50 mg of the compound of formula I or a non-toxic salt thereof. Parenteral unit dosage forms contain from 0.1 to 10 mg of the compound of formula I or a non-toxic salt thereof per 1 ml of the preparation.

The invention is further illustrated by the following Examples of compositions in which all parts are by weight.

EXAMPLE I

A mixture of one part 2-[2-(5-chloro-2,3-dihydrobenzofuranyl)]-2-imidazoline hydrochloride and four parts microcrystalline cellulose together with 1% of magnesium stearate is compressed into tablets. Conveniently the tablets are of such a size as to contain 10, 25 or 50 mg of the active ingredient.

EXAMPLE II

A mixture of one part 2-[2-(5-chloro-2,3-dihydrobenzofuranyl)]-2-imidazoline hydrochloride and four parts spray dried lactose together with 1% magnesium stearate is filled into hard geletin capsules. The capsules may conveniently contain 10, 25 or 50 mg of the active ingredient.

EXAMPLE III

The active ingredient of each of Examples I and II may be replaced by 2-[2-(2,3-dihydrobenzofuranyl)]-2-imidazoline hydrochloride.

We claim:
1. A compound of the formula

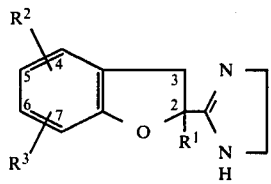

(I)

wherein $R^1$ is hydrogen or alkyl $C_{1-6}$; $R^2$ is hydrogen, methyl, chloro, bromo or fluoro; $R^3$ is hydrogen, methyl, hydroxy, methoxy, fluoro, chloro or bromo; or a non-toxic salt thereof.

2. A compound of formula I given in claim 1 wherein $R^1$ is hydrogen or alkyl $C_{1-6}$; $R^2$ is hydrogen and $R^3$ is methyl, hydroxy, methoxy, fluoro, chloro or bromo; or $R^2$ and $R^3$ are the same and both are hydrogen, methyl or chloro; or a non-toxic salt thereof.

3. 2-[2-(2-Methyl-2,3-dihydrobenzofuranyl)]-2-imidazoline or a non-toxic salt thereof.

4. 2-[2-(5-Chloro-2,3-dihydrobenzofuranyl)]-2-imidazoline or a non-toxic salt thereof.

5. 2-[2-(2,3-Dihydrobenzofuranyl)]-2-imidazoline or a non-toxic salt thereof.

6. A compound according to claim 1 which is selected from the group consisting of 2-[2-(4-chloro-2,3-dihydrobenzofuranyl)]-2-imidazoline, 2-[2-(7-methyl-2,3-dihydrobenzofuranyl)]-2-imidazoline, 2-[2-(5-chloro-7-methyl-2,3-dihydrobenzofuranyl)]-2-imidazoline, 2-[2-(5-fluoro-2,3-dihydrobenzofuranyl)]-2-imidazoline, 2-[2-(5-methoxy-2,3-dihydrobenzofuranyl)]-2-imidazoline, 2-[2-(5-hydroxy-2,3-dihydrobenzofuranyl)]-2-imidazoline, 2-[2-(4-methyl-2,3-dihydrobenzofuranyl)]-2-imidazoline, 2-[2-(5-methyl-2,3-dihydrobenzofuranyl)]-2-imidazoline, 2-[2-(5-bromo-2,3-dihydrobenzofuranyl)]-2-imidazoline, 2-[2-(6-methyl-2,3-dihydrobenzofuranyl)]-2-imidazoline, 2-[2-(6-methoxy-2,3-dihydrobenzofuranyl)]-2-imidazoline, 2-[2-(7-methoxy-2,3-dihydrobenzofuranyl)]-2-imidazoline, 2-[2-(7-chloro-2,3-dihydrobenzofuranyl)]-2-imidazoline, 2-[2-(4,7-dimethyl-2,3-dihydrobenzofuranyl)]-2-imidazoline, 2-[2-(5,6-dimethyl-2,3-dihydrobenzofuranyl)]-2-imidazoline, 2-[2-(5,7-dimethyl-2,3-dihydrobenzofuranyl)]-2-imidazoline, 2-[2-(5,7-dichloro-2,3-dihydrobenzofuranyl)]-2-imidazoline, 2-[2-(6,7-dichloro-2,3-dihydrobenzofuranyl)]-2-imidazoline, 2-[2-(6-hydroxy-2,3-dihydrobenzofuranyl)]-2-imidazoline and 2-[2-(7-hydroxy-2,3-dihydrobenzofuranyl)]-2-imidazoline or a non-toxic salt thereof.

7. A pharmaceutical composition for presynaptic $\alpha_2$-adrenoreceptor antagonist use comprising a compound as claimed in claim 1, or a non-toxic salt thereof in an amount effective for said use together with a pharmaceutically acceptable diluent or carrier.

8. A pharmaceutical composition as claimed in claim 7 which is in unit dosage form.

9. A pharmaceutical composition as claimed in claim 8 for oral administration wherein each unit dosage contains from 1 to 200 mg of the compound of formula I or a non-toxic salt thereof.

10. A pharmaceutical composition as claimed in claim 9 wherein each unit dosage contains from 10 to 50 mg of the compound of formula I or a non-toxic salt thereof.

11. A pharmaceutical composition as claimed in claim 8 for parenteral administration wherein each unit dosage contains from 0.1 to 10 mg of the compound of formula I or a non-toxic salt thereof per 1 ml of the composition.

12. A method of treating depression which comprises administering to a human an antidepressant effective amount of a compound as claimed in claim 1 or a non-toxic salt thereof.

13. A method of treating migraine which comprises administering to a human an antimigraine effective amount of a compound as claimed in claim 1 or a non-toxic salt thereof.

* * * * *